(12) United States Patent
Bathe et al.

(10) Patent No.: US 7,981,897 B2
(45) Date of Patent: Jul. 19, 2011

(54) CRYSTAL FORM OF (3-CYANO-1H-INDO1-7-YL)-[4-(4-FLUOROPHENETHYL)-PIPERAZIN-1-YL]METHANONE, HYDROCHLORIDE

(75) Inventors: Andreas Bathe, Darmstadt (DE); Bernd Helfert, Ober-Ramstadt (DE); Ralf Knierieme, Gross-Zimmern (DE); Christoph Saal, Otzberg (DE); Ronald Keiner, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 500 days.

(21) Appl. No.: 11/576,086

(22) PCT Filed: Sep. 8, 2005

(86) PCT No.: PCT/EP2005/009647
§ 371 (c)(1),
(2), (4) Date: Mar. 27, 2007

(87) PCT Pub. No.: WO2006/034774
PCT Pub. Date: Apr. 6, 2006

(65) Prior Publication Data
US 2007/0259885 A1    Nov. 8, 2007

(30) Foreign Application Priority Data
Sep. 28, 2004 (DE) .......................... 10 2004 047 517

(51) Int. Cl.
*A61K 31/497* (2006.01)
*C07D 403/06* (2006.01)

(52) U.S. Cl. ................... 514/254.09; 544/373
(58) Field of Classification Search .................. 544/373; 514/254.09
See application file for complete search history.

(56) References Cited

U.S. PATENT DOCUMENTS

| 6,838,461 B1 * | 1/2005 | Boettcher et al. ........ 514/254.09 |
| 7,084,143 B2 | 8/2006 | Boettcher et al. |
| 2005/0014766 A1 | 1/2005 | van Amsterdam et al. |

FOREIGN PATENT DOCUMENTS

| WO | WO 01/07435 A | 2/2001 |
| WO | WO 02/059092 A | 8/2002 |
| WO | WO 03/045392 A | 4/2004 |

OTHER PUBLICATIONS

Brittain "Polymorphism in Pharmaceutical Solids", vol. 95, Drugs and Pharmaceutical Sciences, 1999.*
Amamec R. et al., Prophylactic And Therapeutic Effects Of Acute Systemic Injections Of Emd 281014, A Selective Serotonin 2a Receptor Antagonist On Anxiety Induced By Predator Stress In Rats, European Journal of Pharmacology, Nov. 3, 2004, Amsterdam, NL.

* cited by examiner

*Primary Examiner* — James O Wilson
*Assistant Examiner* — Ebenezer Sackey
(74) *Attorney, Agent, or Firm* — Millen, White, Zelano & Branigan, P.C.

(57) ABSTRACT

The present invention relates to a hitherto unknown crystal form B of (3-cyano-1H-indol-7-yl)-[4-(4-fluorophenethyl)-piperazin-1-yl]methanone, hydrochloride, to a process for the preparation thereof, and to the use thereof for the preparation of a medicament.

30 Claims, 4 Drawing Sheets

Figure 1:
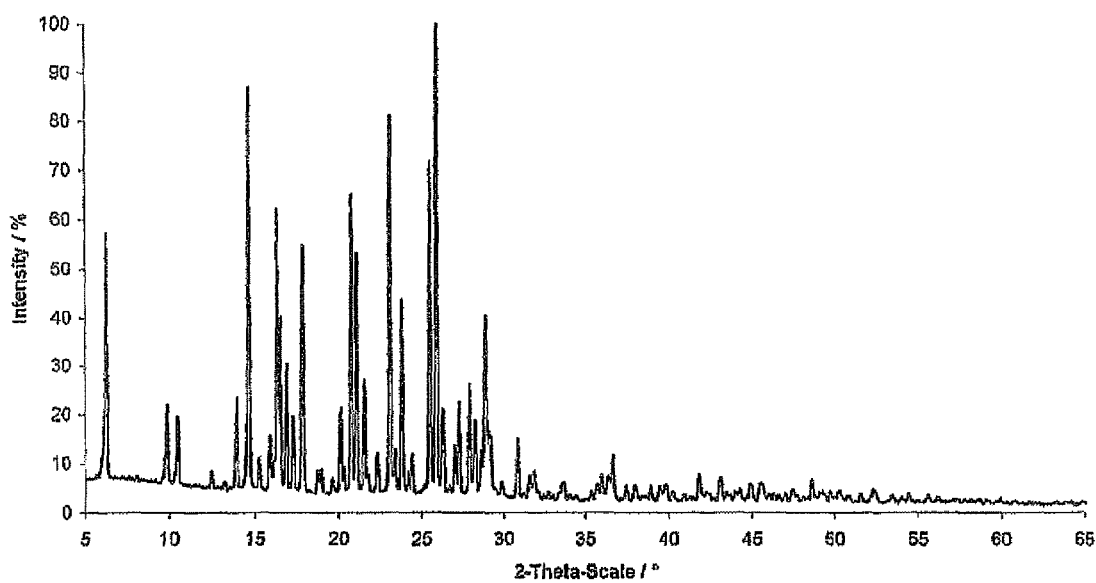

X-ray powder diffraction pattern of crystal form A of EMD281014

X-ray powder diffraction pattern of crystal form B of EMD281014

X-ray powder diffraction pattern of the mixture of crystal forms A and B as obtained in Example 4a X-ray powder diffraction pattern of the mixture of crystal forms A and B as obtained in Example 4b

CRYSTAL FORM OF (3-CYANO-1H-INDO1-7-YL)-[4-(4-FLUOROPHENETHYL)-PIPERAZIN-1-YL]METHANONE, HYDROCHLORIDE

The present invention relates to a hitherto unknown crystal form B of (3-cyano-1H-indol-7-yl)-[4-(4-fluorophenethyl) piperazin-1-yl]methanone, hydrochloride (referred to below as EMD281014), to a process for the preparation thereof, and to the use thereof for the preparation of a medicament.

BACKGROUND OF THE INVENTION

The compound EMD281014 is known from European Patent EP 1 198 453 B1 and has the following structure:

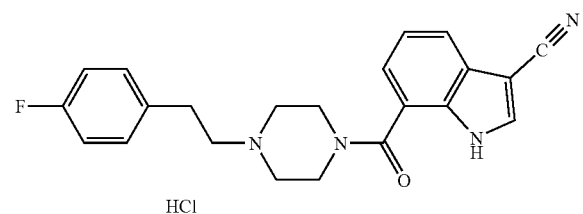

EMD281014 exhibits, inter alia, effects on the central nervous system while being well tolerated and at the same time has valuable pharmacological properties. Thus, the substance has strong affinity to 5-$HT_{2A}$ receptors, while having 5-$HT_{2A}$ receptor-antagonistic properties.

A number of medical uses of EMD281014, for example the treatment of schizophrenia and sleeping disorders, are described in EP 1 198 453 B1. Further medical uses are the subject-matter of WO 03/45392 and WO 04/32932.

Processes for the preparation of EMD0281014 are disclosed in European Patents 1 198 453 B1 and 1 353 906 B1.

As the final process step in each case, the hydrochloride is precipitated from a solution of the free base by addition of an aqueous HCl solution and is separated off from the reaction mixture.

This known procedure always gives a crystal form A, which is characterised by the lattice spacing indicated in Table I, determined by X-ray powder diffraction.

Surprisingly, the inventors of the present patent application have found that a second crystal form B is formed on pressing of EMD281014 to give tablets under mechanical pressure and is present in significant amounts besides form A in the tablets produced. The amount of form B formed depends on the pressing pressure used.

It is extremely disadvantageous for a medicament tablet to comprise a plurality of crystal forms of an active ingredient alongside one another if these crystal forms have different bioavailabilities, for example if they dissolve at different rates under physiological conditions. Even slight variations in the production conditions would then cast doubt on the reproducibility of the bioavailability.

The object of the present invention was therefore to provide EMD281014 in a form which does not change its properties under the tabletting conditions and is therefore suitable for the production of tablets of defined and constant quality.

DESCRIPTION OF THE INVENTION

Surprisingly, it has been found that EMD281014 as a solid can exist in various crystal modifications. Furthermore, it has been found that the crystallisation process and thus the preferential formation of one of the two forms A or B can be controlled through a suitable choice of the process parameters. It is also possible to convert form A into form B and form B into form A without needing to bring EMD281014 into solution for this purpose. Form B should be regarded as stable under the tablet production conditions. It is not possible unambiguously to identify fractions of form A or of further polymorphic forms of EMD281014 in the X-ray diffraction patterns of tablets produced from form B.

Both crystal forms comprise exclusively EMD281014, i.e. neither water nor other solvent molecules.

As already mentioned, form A is obtained by the preparation processes known from the prior art. Form A is characterised by X-ray data as shown in Table I.

TABLE I

Reflection positions of EMD281014 form A

| No. | d [Å] | Error range d [Å] | I/$I_0$ |
|---|---|---|---|
| 1 | 14.132 | ±0.25 | 53 |
| 2 | 8.939 | ±0.10 | 17 |
| 3 | 6.304 | ±0.05 | 19 |
| 4 | 6.013 | ±0.05 | 85 |
| 5 | 5.388 | ±0.05 | 60 |
| 6 | 5.293 | ±0.05 | 37 |
| 7 | 5.193 | ±0.05 | 27 |
| 8 | 4.927 | ±0.05 | 52 |
| 9 | 4.369 | ±0.05 | 18 |
| 10 | 4.224 | ±0.05 | 63 |
| 11 | 4.167 | ±0.02 | 50 |
| 12 | 4.078 | ±0.02 | 23 |
| 13 | 3.812 | ±0.02 | 79 |
| 14 | 3.691 | ±0.02 | 41 |
| 15 | 3.434 | ±0.02 | 71 |
| 16 | 3.383 | ±0.02 | 100 |
| 17 | 3.330 | ±0.02 | 17 |
| 18 | 3.207 | ±0.02 | 19 |
| 19 | 3.134 | ±0.02 | 23 |
| 20 | 3.027 | ±0.02 | 38 |

Measurement conditions: Transmission mode, generator power 40 kV/30 mA, Cu-Kα1 radiation (λ=1.54056 Å), position-sensitive detector (3.3 kV), measurement range: 3-65°2θ, step size: 0.05°θ, time/step: 1.4 s Evaluation: The diffraction patterns were background-corrected throughout the recording range 3-65°2θ, and the reflection intensities were determined for the 20 strongest reflections in each case. The angle position tolerance is ±0.1°2θ for the Cu-Kα1 radiation used.

In order to prepare form B in high yield and essentially in pure form, the following procedure is followed:

Firstly, the free base of EMD281014 is prepared in a manner known per se and subsequently dried thermally in order to remove adhering solvents. Instead of then precipitating the hydrochloride by addition of an aqueous HCl solution, HCl gas is passed through a solution of the free base. This likewise gives a precipitate, which, however, surprisingly does not consist of form A, but of B.

The term "form B, essentially pure" or "essentially consisting of form B" here is taken to mean that form B comprises less than 5%, preferably less than 2% and very preferably less than 1% of form A.

Form B is characterised by X-ray data as shown in Table II.

TABLE II

Reflection positions of EMD281014 form B

| No. | d [Å] | Error range d [Å] | I/I$_0$ |
|---|---|---|---|
| 1 | 13.083 | ±0.20 | 30 |
| 2 | 6.688 | ±0.10 | 77 |
| 3 | 5.669 | ±0.05 | 55 |
| 4 | 5.292 | ±0.05 | 100 |
| 5 | 4.786 | ±0.05 | 41 |
| 6 | 4.040 | ±0.02 | 46 |
| 7 | 3.881 | ±0.02 | 28 |
| 8 | 3.514 | ±0.02 | 37 |
| 9 | 3.239 | ±0.02 | 28 |
| 10 | 3.200 | ±0.02 | 25 |

Measurement conditions and evaluation are carried out as described for Table I.

In a preferred embodiment, form B is characterised by X-ray data as shown in Table IIa. The data as shown in Table IIa contain the reflections from table II and in addition 10 further reflections of lower intensity.

TABLE IIa

Reflection positions of EMD281014 form B

| No. | d [Å] | Error range d [Å] | I/I$_0$ |
|---|---|---|---|
| 1 | 13.083 | ±0.20 | 30 |
| 2 | 8.706 | ±0.10 | 19 |
| 3 | 6.688 | ±0.10 | 77 |
| 4 | 6.499 | ±0.05 | 19 |
| 5 | 5.669 | ±0.05 | 55 |
| 6 | 5.292 | ±0.05 | 100 |
| 7 | 4.786 | ±0.05 | 41 |
| 8 | 4.322 | ±0.05 | 23 |
| 9 | 4.040 | ±0.02 | 46 |
| 10 | 3.881 | ±0.02 | 28 |
| 11 | 3.595 | ±0.02 | 14 |
| 12 | 3.514 | ±0.02 | 37 |
| 13 | 3.435 | ±0.02 | 22 |
| 14 | 3.337 | ±0.02 | 14 |
| 15 | 3.289 | ±0.02 | 25 |
| 16 | 3.239 | ±0.02 | 28 |
| 17 | 3.200 | ±0.02 | 25 |
| 18 | 3.143 | ±0.02 | 18 |
| 19 | 3.073 | ±0.02 | 22 |
| 20 | 2.867 | ±0.01 | 19 |

Measurement conditions and evaluation are carried out as described for Table I.

The present invention accordingly relates to a polymorphic crystal form B of EMD281014, characterised by the characteristic interlattice plane distances indicated in Table II.

In particular, the present invention relates to a polymorphic crystal form B of EMD281014, characterised by the characteristic interlattice plane distances indicated in Table IIa.

The invention furthermore relates to a process for the preparation of crystal form B of EMD281014 from a solution of the free base of EMD281014, characterised in that HCl gas is passed through this solution, and the precipitate which forms is separated off.

In general, molar excesses of solvent to dissolved substance of from 50:1 to 200:1, but preferably from 100:1 to 150:1, are used here. A preferred solvent is tetrahydrofuran (THF).

It has furthermore been found that form B can also be obtained by stirring a suspension of crystals of form A in tert-butyl methyl ether (MTBE).

The present invention therefore likewise relates to a corresponding preparation process.

If the process is carried out at room temperature for 14 days, about 30% of form B are obtained in addition to form A, where the ratio of B to A is estimated by comparison of the X-ray powder diffraction pattern of the mixture with the diffraction patterns of the pure substances. The choice of shorter or longer reaction times enables the preparation of mixtures of B and A in any desired compositions. The present invention therefore relates to EMD281014 comprising form B.

Mixtures which are preferred in accordance with the invention comprise in each case more than 10%, 20%, 30%, 40%, 50%, 60%, 70%, 80% or 90% of form B. The invention furthermore relates to EMD281014 which essentially consists of form B.

It is likewise possible to prepare form A by stirring a suspension of crystals of form B. In this case, polar solvents, such as, for example, acetone, water or mixtures of these two solvents, are employed. A preferred mixture here is acetone/water in a ratio of 55:45% by weight. If water is used as the sole solvent, the process is preferably carried out at acidic pH (in particular pH 1).

The present invention therefore likewise relates to a corresponding preparation process.

As already mentioned, form B is formed from form A under the action of pressure. The present invention therefore furthermore relates to a process for the preparation of crystal form B of EMD281014, characterised in that mechanical pressure is exerted on crystals of form A.

The pressures here are preferably those which usually prevail during tablet production if ram forces of between about 2 and 16 kN, in particular between 6 and 16 kN, are used as the maximum pressing forces. It has been observed that the proportion of form B increases with increasing pressure. In a tabletting operation in a cam press with a duration (contact time) of 310 ms and a maximum pressing force of 16 kN, a mixture of about 25% of form B and 75% of form A is obtained. In a tabletting operation in a cam press with a contact time of 250 ms and a maximum pressing force of 6 kN, the proportion is about 20% of B.

Furthermore, a very simple method for the preparation of form A from form B has been found. To this end, form B merely needs to be stored at elevated temperatures of between about 75 and about 225° C., preferably 90 and 160° C. and particularly preferably between 110 and 140° C. Depending on the temperature and the storage duration, different degrees of conversion can be achieved. Depending on the target degree of conversion, the storage duration at a given temperature can be between a few minutes and several days. In order to achieve high degrees of conversion, form A is preferably stored for from several hours to days. Suitable storage times are, for example, 4, 8, 12, 16, 20, 24, 36 or 48 hours. At 105° C., complete conversion of B into A can be achieved, for example, by storage for a period of 24 hours.

The present invention likewise relates to a corresponding preparation process of A from B.

Finally, the present invention relates to the use of form B as medicament or for the preparation of pharmaceutical compositions and medicaments and to these compositions and medicaments as such.

The said use takes place analogously to the known form A as described in EP 1 198 453 B1, WO 03/45392 and WO 04/32932.

EXAMPLES

1. Preparation of Form B of EMD281014 from a Solution of the Free Base 50 g of the base (3-cyano-1H-indol-7-yl)-[4-(4-fluorophenethyl)piperazin-1-yl]methanone on which EMD281014 is based are dissolved in 1400 ml of THF in a 2 litre round-bottomed flask. The mixture is subsequently cooled to 5° C. 20 g of HCl gas (corresponding to a molar excess of 4.1, based on the base employed) are then passed in over the course of 4 minutes with cooling by means of an ice/ethanol bath. A white precipitate forms. When the reaction is complete, the batch is stirred at 25 to 27° C. for a further 60 minutes. The precipitate is subsequently filtered off at this temperature via a Büchner funnel and dried for 18 hours at 23° C. in a vacuum drying cabinet, giving 53.3 g of white, solid crystals (yield: 97% of theory), which correspond to crystal form B (determination via X-ray powder diffraction pattern).

The crystals obtained in this way have characteristic inter-lattice plane distances, as indicated in Table II and/or IIa. For further characterisation, a Raman spectrum is recorded, which shows the typical bands listed in Table III.

TABLE III

Raman bands of EMD281014 form B

| Wavenumber [cm$^{-1}$] | Intensity |
| --- | --- |
| 3075 ± 1.5 | M |
| 3066 ± 1.5 | M |
| 3057 ± 1.5 | M |
| 2994 ± 1.5 | M |
| 2961 ± 1.5 | M |
| 2927 ± 1.5 | M |
| 2219 ± 1.5 | S |
| 1629 ± 1.5 | M |
| 1611 ± 1.5 | M |
| 1604 ± 1.5 | W |
| 1594 ± 1.5 | W |
| 1525 ± 1.5 | M |
| 1447 ± 1.5 | M |
| 1342 ± 1.5 | M |
| 1333 ± 1.5 | M |
| 1298 ± 1.5 | M |
| 1250 ± 1.5 | M |
| 1160 ± 1.5 | M |
| 858 ± 1.5 | M |
| 826 ± 1.5 | M |
| 689 ± 1.5 | M |
| 637 ± 1.5 | M |
| 627 ± 1.5 | M |
| 503 ± 1.5 | M |

Measurement conditions: FT Raman spectroscopy, Bruker RFS100, 1064 nm excitation, 750 mW, 1 cm$^{-1}$ spectral resolution, 250 scans.

Evaluation: The Raman spectrum obtained is vector-standardised in the spectral range 3600-250 cm$^{-1}$. The bands are classified on the basis of their intensity as follows into S=strong, M=moderate and W=weak:

| | |
| --- | --- |
| S | I > 0.075 |
| M | 0.01 < I < 0.075 |
| W | I < 0.01 |

2. Comparative Example

Preparation of Form A of EMD281014 from a Solution of the Free Base as Described in EP 1 353 906 B1

2.1 g of the free base of EMD281014 are heated in 50 ml of acetone, and water is added until a clear solution is formed. A mixture of 0.6 ml of hydrochloric acid (w=37%) and 1.2 ml of acetone is then stirred in. The mixture is subsequently evaporated to half the volume in a rotary evaporator. The precipitated hydrochloride is filtered off with suction, washed with acetone and diethyl ether and dried, giving 1.6 g of 7-{4-[2-(4-fluorophenyl)ethyl]-piperazine-1-carbonyl}-1H-indole-3-carbonitrile, hydrochloride (69% of theory), decomposition range 314-319°.

The crystals obtained in this way have characteristic inter-lattice plane distances as indicated in Table II and/or IIa. For further characterisation, a Raman spectrum is recorded, which shows the typical bands listed in Table IV.

TABLE IV

Raman bands of EMD281014 form A

| Wavenumber [cm$^{-1}$] | Intensity |
| --- | --- |
| 3083 ± 1.5 | M |
| 3068 ± 1.5 | M |
| 3058 ± 1.5 | M |
| 3007 ± 1.5 | M |
| 2990 ± 1.5 | M |
| 2960 ± 1.5 | M |
| 2941 ± 1.5 | M |
| 2224 ± 1.5 | S |
| 1634 ± 1.5 | M |
| 1613 ± 1.5 | M |
| 1602 ± 1.5 | M |
| 1596 ± 1.5 | M |
| 1530 ± 1.5 | S |
| 1441 ± 1.5 | M |
| 1345 ± 1.5 | M |
| 1331 ± 1.5 | M |
| 1294 ± 1.5 | M |
| 1246 ± 1.5 | M |
| 1157 ± 1.5 | M |
| 859 ± 1.5 | M |
| 831 ± 1.5 | M |
| 824 ± 1.5 | M |
| 691 ± 1.5 | M |
| 638 ± 1.5 | M |
| 625 ± 1.5 | W |
| 505 ± 1.5 | W |
| 499 ± 1.5 | W |

Measurement conditions and evaluation are as described in Table III.

3. Preparation of Form B of EMD281014 from Form A by Stirring a Suspension of A in MTBE 250 mg of EMD281014 form A are dispersed in 5 ml of MTBE and stirred for 14 days at room temperature in a sealed brown-glass vessel, The residue is filtered off via a circular paper filter and dried in room air. Result of the X-ray diffraction measurement: a mixture of EMD281014 form A and form B is present. The proportion of form B is estimated as about 30% by weight by comparison of the X-ray powder diffraction patterns of the pure forms.

4. Preparation of Form B from Form A by Application of Pressure

In an EK0 cam press from Korsch (Berlin, Germany), year of construction 2002, tablets are produced at a rate of 50 units per minute using a 7 mm, round, flat ram with bevel.

The tablets contain 50 mg of EMD281014 in crystal form A, 93.2 mg of lactose monohydrate, 4.5 mg of croscarmellose and 2.3 mg of magnesium stearate. The ingredients are dry-mixed and compressed directly.

Figure 2:
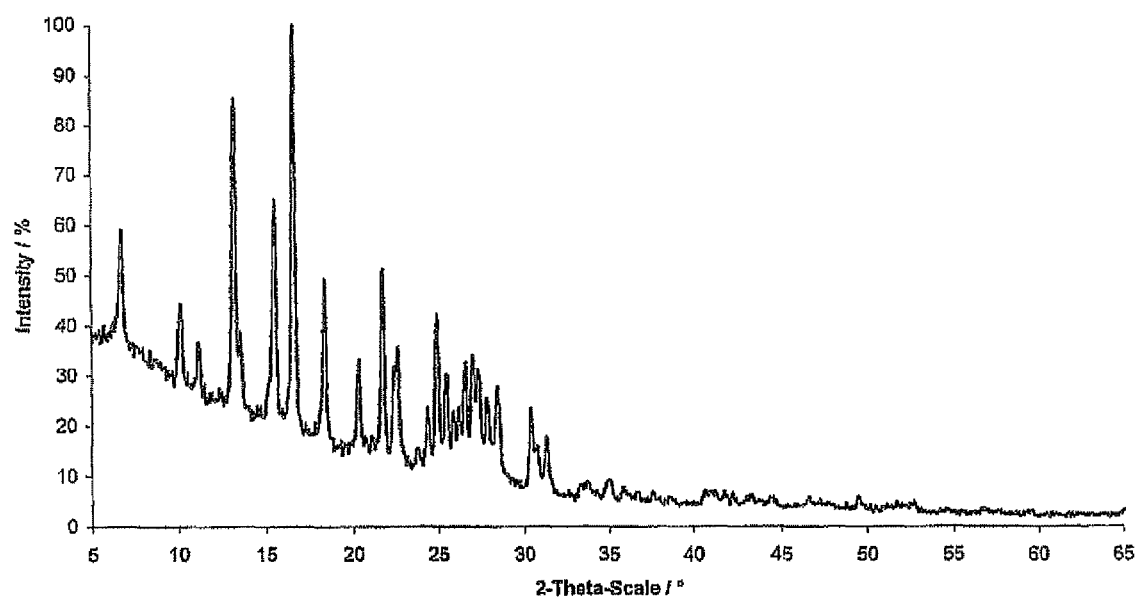
Figure 3:
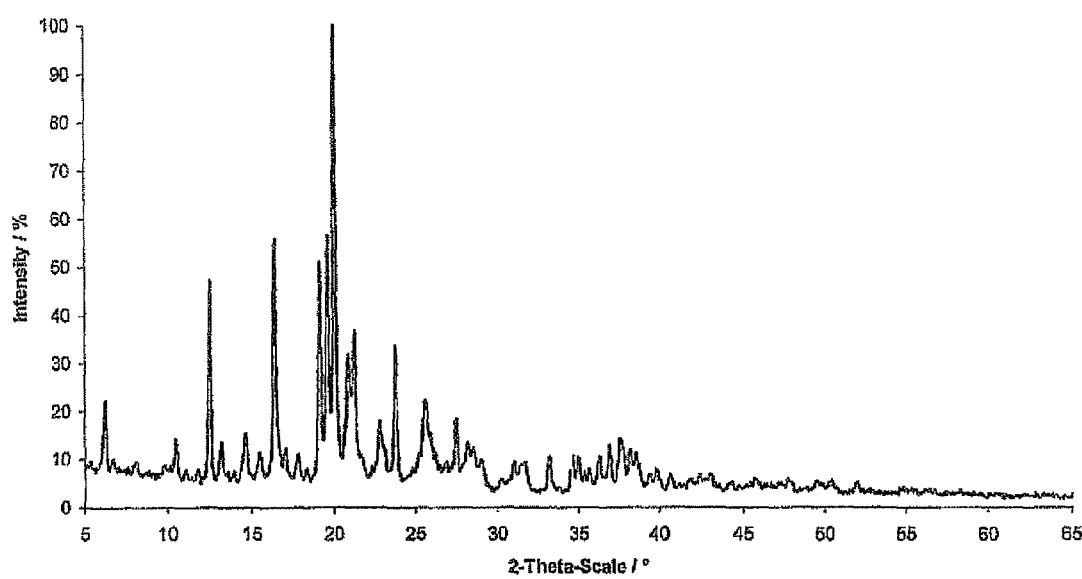
Figure 4:
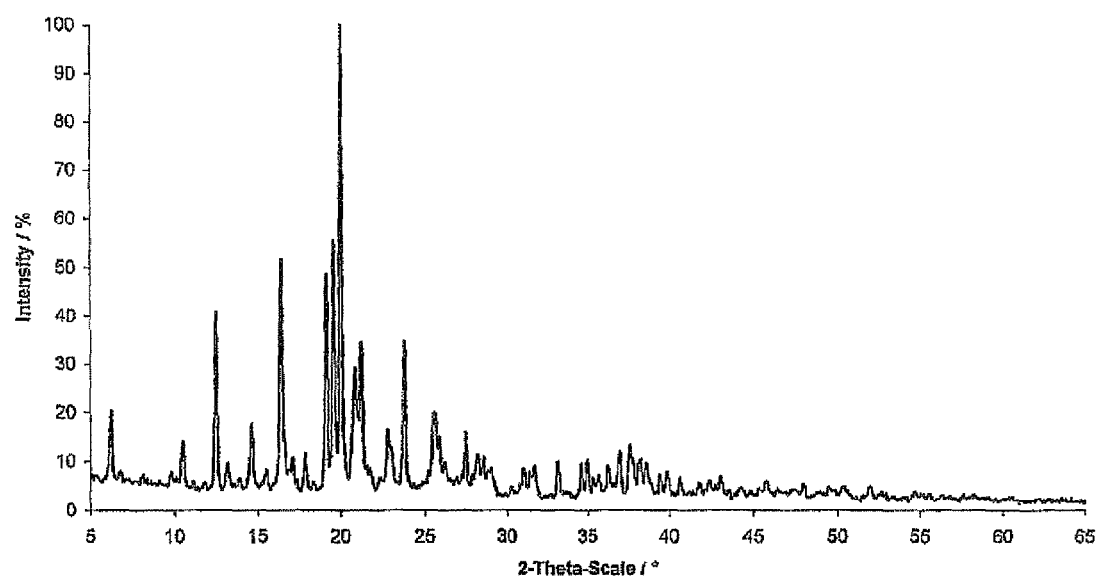

The proportion of form B is estimated by comparison of the X-ray powder diffraction patterns of the mixtures (FIGS. 3 and 4) with the diffraction patterns of the pure forms (FIGS. 1 and 2).

The following results are obtained:

| | Example | |
|---|---|---|
| | 4a | 4b |
| Mean maximum upper ram force [kN] | 16 | 6 |
| Area under pressing force curve [kN ms] | 2780 | 800 |
| Contact time [ms] | 310 | 270 |
| Proportion of form B | 25 | 20 |

The invention claimed is:

1. Crystal form B of (3-cyano-1H-indol-7-yl)-[4-(4-fluorophenethyl)piperazin-1-yl]methanone, hydrochloride, having the following characteristic interlattice plane distances in Å: 13.083±0.20, 6.688±0.10, 5.669±0.05, 5.292±0.05, 4.786±0.05, 4.040±0.02, 3.881±0.02, 3.514±0.02, 3.239±0.02, and 3.200±0.02.

2. Crystal form B of (3-cyano-1H-indol-7-yl)-[4-(4-fluorophenethyl)piperazin-1-yl]methanone, hydrochloride, according to claim 1, having the following characteristic interlattice plane distances in Å: 13.083±0.20, 8.706±0.10, 6.688±0.10, 6.499±0.05, 5.669±0.05, 5.292±0.05, 4.786±0.05, 4.322±0.05, 4.040±0.02, 3.881±0.02, 3.595±0.02, 3.514±0.02, 3.435±0.02, 3.337±0.02, 3.289±0.02, 3.239±0.02, 3.200±0.02, 3.143±0.02, 3.073±0.02, and 2.867±0.01.

3. A composition comprising (3-Cyano-1H-indol-7-yl)-[4-(4-fluorophenethyl)piperazin-1-yl]methanone, hydrochloride crystal form A and (3-Cyano-1H-indol-7-yl)-[4-(4-fluorophenethyl)piperazin-1-yl]methanone, hydrochloride crystal form B according to claim 1.

4. (3-Cyano-1H-indol-7-yl)-[4-(4-fluorophenethyl)piperazin-1-yl]methanone, hydrochloride, consisting essentially of crystal form B according to claim 1.

5. A process for the preparation of crystal form B according to claim 1 from form A, said process comprising exerting mechanical pressure on form A of (3-Cyano-1H-indol-7-yl)-[4-(4-fluorophenethyl)piperazin-1-yl]methanone, hydrochloride.

6. A process for the preparation of crystal form B according to claim 1, said process comprising passing HCl gas through a solution of (3-cyano-1H-indol-7-yl)-[4-(4-fluorophenethyl)piperazin-1-yl]methanone, separating off the precipitate which forms from the reaction mixture, and drying said precipitate.

7. A process for the preparation of crystal form B according to claim 1, said process comprising stirring a suspension of crystals of form A in tert-butyl methyl ether, separating off the residue from the reaction mixture, and drying said residue.

8. Crystal form B of (3-cyano-1H-indol-7-yl)-[4-(4-fluorophenethyl)piperazin-1-yl]methanone, hydrochloride, obtainable by a process according to claim 5.

9. A pharmaceutical composition comprising crystal form B of (3-cyano-1H-indol-7-yl)-[4-(4-fluorophenethyl)piperazin-1-yl]methanone, hydrochloride according to claim 1 and one or more further active ingredients and/or adjuvants.

10. A method of treating a patient suffering from schizophrenia comprising administering to said patient an effective amount of crystal form B of (3-cyano-1H-indol-7-yl)-[4-(4-fluorophenethyl)piperazin-1-yl]methanone, hydrochloride according to claim 1.

11. A process for the preparation of the known crystal form A from crystal form B according to claim 1, said process comprising storing form B at an elevated temperature of from about 75 to about 225° C.

12. A process for the preparation of the known crystal form A from crystal form B according to claim 1, said process comprising stirring a suspension of crystals of form B in a polar solvent or solvent mixture, separating off the residue from the reaction mixture, and drying said residue.

13. A composition comprising (3-Cyano-1H-indol-7-yl)-[4-(4-fluorophenethyl)piperazin-1-yl]methanone, hydrochloride crystal form A and (3-Cyano-1H-indol-7-yl)-[4-(4-fluorophenethyl)piperazin-1-yl]methanone, hydrochloride crystal form B according to claim 2.

14. (3-Cyano-1H-indol-7-yl)-[4-(4-fluorophenethyl)piperazin-1-yl]methanone, hydrochloride, consisting essentially of crystal form B according to claim 2.

15. Crystal form B of (3-cyano-1H-indol-7-yl)-[4-(4-fluorophenethyl)piperazin-1-yl]methanone, hydrochloride, obtainable by a process according to claim 6.

16. Crystal form B of (3-cyano-1H-indol-7-yl)-[4-(4-fluorophenethyl)piperazin-1-yl]methanone, hydrochloride, obtainable by a process according to claim 7.

17. A process for the preparation of crystal form B according to claim 2 from form A, said process comprising exerting mechanical pressure on form A of (3-Cyano-1H-indol-7-yl)-[4-(4-fluorophenethyl)piperazin-1-yl]methanone, hydrochloride.

18. A process for the preparation of crystal form B according to claim 2, said process comprising passing HCl gas through a solution of (3-cyano-1H-indol-7-yl)-[4-(4-fluorophenethyl)piperazin-1-yl]methanone, separating off the precipitate which forms from the reaction mixture, and drying said precipitate.

19. A process for the preparation of crystal form B according to claim 2, said process comprising stirring a suspension of crystals of form A in tert-butyl methyl ether, separating off the residue from the reaction mixture, and drying said residue.

20. Crystal form B of (3-cyano-1H-indol-7-yl)-[4-(4-fluorophenethyl)piperazin-1-yl]methanone, hydrochloride, obtainable by a process according to claim 17.

21. Crystal form B of (3-cyano-1H-indol-7-yl)-[4-(4-fluorophenethyl)piperazin-1-yl]methanone, hydrochloride, obtainable by a process according to claim 18.

22. Crystal form B of (3-cyano-1H-indol-7-yl)-[4-(4-fluorophenethyl)piperazin-1-yl]methanone, hydrochloride, obtainable by a process according to claim 19.

23. A method of treating a patient suffering from a sleeping disorder comprising administering to said patient an effective amount of the crystal form according to claim 1.

24. A process according to claim 6, wherein in said solution of (3-cyano-1H-indol-7-yl)-[4-(4-fluorophenethyl)piperazin-1-yl]methanone, the molar excess of solvent to dissolved substance is from 50:1 to 200:1, and the solvent is tetrahydrofuran (THF).

25. A process according to claim 5, wherein said mechanical pressure exerted on form A of (3-Cyano-1H-indol-7-yl)-[4-(4-fluorophenethyl)-piperazin-1-yl]methanone, hydrochloride is between about 2 and 16 kN.

26. A process according to claim 5, wherein said mechanical pressure exerted on form A of (3-Cyano-1H-indol-7-yl)-

[4-(4-fluorophenethyl)-piperazin-1-yl]methanone, hydrochloride is between 6 and 16 kN.

27. A process according to claim 11, wherein form B is stored at elevated temperatures of between about 75 and about 225° C. for 4-48 hours.

28. Crystal form B of (3-cyano-1H-indol-7-yl)-[4-(4-fluorophenethyl)-piperazin-1-yl]methanone, hydrochloride, having an X-ray diffraction pattern comprising the following characteristic interlattice plane distances in Å: 13.083±0.20, 6.688±0.10, and 5.669±0.05.

29. The crystal form B of (3-cyano-1H-indol-7-yl)-[4-(4-fluorophenethyl)piperazin-1-yl]methanone, hydrochloride, according to claim 28, wherein said X-ray diffraction pattern further comprises the following characteristic interlattice plane distances in Å: 5.292±0.05, 4.786±0.05, 4.040±0.02, 3.881±0.02, 3.514±0.02, 3.239±0.02, and 3.200±0.02.

30. The crystal form B of (3-cyano-1H-indol-7-yl)[4-(4-fluorophenethyl)piperazin-1-yl]methanone, hydrochloride, according to claim 28, wherein said X-ray diffraction pattern further comprises comprising the following characteristic interlattice plane distances in Å: 8.706±0.10, 6.499±0.05, 5.292±0.05, 4.786±0.05, 4.322±0.05, 4.040±0.02, 3.881±0.02, 3.595±0.02, 3.514±0.02, 3.435±0.02, 3.337±0.02, 3.289±0.02, 3.239±0.02, 3.200±0.02, 3.143±0.02, 3.073±0.02, and 2.867±0.01.

\* \* \* \* \*